United States Patent
Cahoon et al.

(12)

(10) Patent No.: US 6,168,951 B1
(45) Date of Patent: Jan. 2, 2001

(54) PLANT GERANYLGERANYL TRANSFERASES

(75) Inventors: Rebecca E. Cahoon; Anthony John Kinney; J. Antoni Rafalski, all of Wilmington, DE (US)

(73) Assignee: E. I. du Pont de Nemours and Company, Wilmington, DE (US)

( * ) Notice: Under 35 U.S.C. 154(b), the term of this patent shall be extended for 0 days.

(21) Appl. No.: 09/387,574

(22) Filed: Aug. 31, 1999

Related U.S. Application Data

(60) Provisional application No. 60/098,743, filed on Sep. 1, 1998.

(51) Int. Cl.[7] ..................................................... C12N 15/54
(52) U.S. Cl. ....................... 435/410; 435/252.3; 435/193; 536/23.2
(58) Field of Search .................................. 435/410, 252.3, 435/193; 536/23.2

(56) References Cited

PUBLICATIONS

Farnsworth, C. et al. (1994) Proc. Natl. Acad. Sci USA 91(25):11963–11967.*
NCBI General Identifier No. 2506788 (1997).*
NCBI General Identifier No. 3355484 (1998).*
NCBI General Identifier No. 2950156 (1998).*
Hum. Mol. Genet. 3(7), 1041–1046 (1994).*

* cited by examiner

*Primary Examiner*—Charles L. Patterson, Jr.

(57) ABSTRACT

This invention relates to an isolated nucleic acid fragment encoding a geranylgeranyl transferase subunit. The invention also relates to the construction of a chimeric gene encoding all or a portion of the geranylgeranyl transferase subunit, in sense or antisense orientation, wherein expression of the chimeric gene results in production of altered levels of the geranylgeranyl transferase subunit in a transformed host cell.

10 Claims, No Drawings

SEQUENCE LISTING

<160> NUMBER OF SEQ ID NOS: 12

<210> SEQ ID NO 1
<211> LENGTH: 1411
<212> TYPE: DNA
<213> ORGANISM: Zea mays
<220> FEATURE:
<221> NAME/KEY: unsure
<222> LOCATION: (785)
<220> FEATURE:
<221> NAME/KEY: unsure
<222> LOCATION: (792)

<400> SEQUENCE: 1

```
gcacgagata ttttgaaata gcccccgcca cgaaattctt cagccatcgt ggaggggttc     60
agttcagggg aggactcgac tcaggaaaca ggagcacgag cggagcagaa ggcagtcatg    120
gcggatgagg tggagcttgc tgcggaccag cacgtccgct acatcgtcac ggtggagaag    180
aagaaggact cctttgagtc gctggtgatg gagcacatcc gcctcaacgg cgcctactgg    240
ggcctcacca cgctcgacct cctccacaag ctccatgccg tagatgccgc cgaggtcgtc    300
gactggatca tgtcctgcta ccaccccgaa tctggtggat ttggagggaa cgttgggcat    360
gacccgcatg tcctctacac gcttagcgcc gtgcaggtcc tctgcctttt cgatcggctc    420
gatgtccttg acgtcgacaa ggttgctgat tatgtcgccg gactgcaaaa caaggatgga    480
tcatttctg gcgatatttg gggtgaagtt gacactaggt tctcgtatat tgccttatgt    540
accttatcat tactgcaccg tctgcataag attgatgtgc aaaaagctgt ggatttcgtt    600
gttagctgta agaacttgga tggcggattt ggagctatgc caggagggga gtctcatgct    660
ggacaaatat tttgttgtgt cggcgcgctc gcaatcaccg ggtccctgca tcacattgat    720
agagacctcc tcgatggtg gctctgtgag cgccagtgta agacggagg acttaatggg    780
cggcntgaga anctagctga tgtggtttgc tactcgtggt gggtgctatc gagcctagtc    840
atgattgaca gagtgcattg gattgacaag gaaaagctaa cgaaattcat actgaactgt    900
caggacaaag agaacggcgg catttcagat agaccagata atgcagtcga tatctatcac    960
acgtactttg gaattgcagg gctttcatta atggagtacc ccggggtgaa gcctttggat   1020
cctgcctatg cactaccatt gcacgttgtc aatcggattt tcttgaaaaa atagaacatt   1080
ccattcgatc tgcggcgcag agatatgctg agatggcgct gtcagatgtg gacgctactt   1140
cacagaacca cgattcgacg gagaaatagc tgagggggaa tcaattacag aacatgttg    1200
ggataccata atcttggact tgtattctcg cattggctgt ggccgcttag tcgatgtttt   1260
tttgtcattt ggcacttgcc ctgttgaatg cttggtgcat gctgtgtttt gctagttgat   1320
ctgattctct tgtttaagtc gtaacattgt gtgtcctgat gacgacgaca ttagtcagga   1380
gctatctata aacagtatgt cttttttgaa a                                  1411
```

<210> SEQ ID NO 2
<211> LENGTH: 318
<212> TYPE: PRT
<213> ORGANISM: Zea mays
<220> FEATURE:
<221> NAME/KEY: UNSURE
<222> LOCATION: (227)

<400> SEQUENCE: 2

```
Met Ala Asp Glu Val Glu Leu Ala Ala Asp Gln His Val Arg Tyr Ile
 1               5                  10                  15
```

-continued

```
Val Thr Val Glu Lys Lys Asp Ser Phe Glu Ser Leu Val Met Glu
             20                  25                  30

His Ile Arg Leu Asn Gly Ala Tyr Trp Gly Leu Thr Thr Leu Asp Leu
         35                  40                  45

Leu His Lys Leu His Ala Val Asp Ala Ala Glu Val Val Asp Trp Ile
         50                  55                  60

Met Ser Cys Tyr His Pro Glu Ser Gly Gly Phe Gly Gly Asn Val Gly
 65              70                  75                  80

His Asp Pro His Val Leu Tyr Thr Leu Ser Ala Val Gln Val Leu Cys
                 85                  90                  95

Leu Phe Asp Arg Leu Asp Val Leu Asp Val Asp Lys Val Ala Asp Tyr
                100                 105                 110

Val Ala Gly Leu Gln Asn Lys Asp Gly Ser Phe Ser Gly Asp Ile Trp
            115                 120                 125

Gly Glu Val Asp Thr Arg Phe Ser Tyr Ile Ala Leu Cys Thr Leu Ser
130                 135                 140

Leu Leu His Arg Leu His Lys Ile Asp Val Gln Lys Ala Val Asp Phe
145                 150                 155                 160

Val Val Ser Cys Lys Asn Leu Asp Gly Gly Phe Gly Ala Met Pro Gly
                165                 170                 175

Gly Glu Ser His Ala Gly Gln Ile Phe Cys Cys Val Gly Ala Leu Ala
                180                 185                 190

Ile Thr Gly Ser Leu His His Ile Asp Arg Asp Leu Leu Gly Trp Trp
            195                 200                 205

Leu Cys Glu Arg Gln Cys Lys Asp Gly Gly Leu Asn Gly Arg Leu Arg
210                 215                 220

Thr Ser Xaa Cys Glu Val Cys Tyr Ser Trp Trp Val Leu Ser Ser Leu
225                 230                 235                 240

Val Met Ile Asp Arg Val His Trp Ile Asp Lys Glu Lys Leu Thr Lys
                245                 250                 255

Phe Ile Leu Asn Cys Gln Asp Lys Glu Asn Gly Gly Ile Ser Asp Arg
            260                 265                 270

Pro Asp Asn Ala Val Asp Ile Tyr His Thr Tyr Phe Gly Ile Ala Gly
            275                 280                 285

Leu Ser Leu Met Glu Tyr Pro Gly Val Lys Pro Leu Asp Pro Ala Tyr
290                 295                 300

Ala Leu Pro Leu His Val Val Asn Arg Ile Phe Leu Lys Lys
305                 310                 315
```

```
<210> SEQ ID NO 3
<211> LENGTH: 1306
<212> TYPE: DNA
<213> ORGANISM: Glycine max

<400> SEQUENCE: 3
gcacgagttt cgcttgacct tggcacaaac taacagagca ttagcgtttc tacttcgtat      60
cactgccgcg acccttctgg attccgacgg tgactttgat taaggagtcc gatgggagag     120
ctggccactg agaaacatgt tcgatatata ttatcagttg aaaagaggaa agataacttt     180
gaatctgtcg taatggagca tctaagaatg aatggggcat attggggatt gaccactctg     240
gatcttctag gaaagcttca taccgtcgat gttgatgagg ttgtttcgtg gttgatgagt     300
tgtcagcatg actcaggggg atttggtgga atgttggac atgatccgca catcctctat     360
acactaagtg ctgtgcaggt gttgtctctc tttgataagc tggatgttat tgatgtagat     420
```

-continued

```
aaggtcacaa gttatattgt cagcctgcaa aatgaagatg gatcctttc aggggatatg      480 tggggtgaag ttgatacacg gttctcatat attgctattt gttgtctatc aatattacat      540
cgcttggata aaatcaatgt ggagaaggct gtgaagtaca ttataagttg caaaaatatg      600
gatggtggtt ttgggtgcac tcctggtggg aatctcatg ctggtcaaat tttctgttgt       660 gtggggccc ttgccataac agggtcacta gatcttgttg acaaagacct acttggttgg       720
tggttatgcg agcgacaggt taaatctgga ggtctgaatg ggcgtcctga gaaacatcct      780
gatgtctgct actcatggtg ggttcttcct agcctgatca tgattgatag gtacattgg       840 attagtaagg agaagcttat aaagttcatc ttagactgcc aggacacaga aatggtgga      900 atttcggaca ggccagatga tgctgtggat gtctttcata cattctttgg ggtggctgga      960
ctttctcttc ttgaatatcc agggctgaaa ccagtagatc cagcttatgc tttacctgtt     1020
gatgttgtaa atagaattat ttttactaaa taaggacttt agtagttaag ttcgatgata     1080
attttccagt aatgacaaaa tcttgggttt gtaagactca ctgttgggag ttggaccccc     1140
tcctcccatc cccagcccaa aaacagttaa tttcttaaaa acagtgttaa catttgagc      1200 ttcttttagt taaattgctg tggtacgaca tgtaaagatt gatcagtatt gtagtcaacc     1260
atcaaattta tgctactagt tactacataa aaaaaaaaa aaaaaa                     1306
```

<210> SEQ ID NO 4
<211> LENGTH: 313
<212> TYPE: PRT
<213> ORGANISM: Glycine max

<400> SEQUENCE: 4

```
Met Gly Glu Leu Ala Thr Glu Lys His Val Arg Tyr Ile Leu Ser Val
  1               5                  10                  15

Glu Lys Arg Lys Asp Asn Phe Glu Ser Val Val Met Glu His Leu Arg
             20                  25                  30

Met Asn Gly Ala Tyr Trp Gly Leu Thr Thr Leu Asp Leu Leu Gly Lys
         35                  40                  45

Leu His Thr Val Asp Val Asp Glu Val Val Ser Trp Leu Met Ser Cys
     50                  55                  60

Gln His Asp Ser Gly Gly Phe Gly Gly Asn Val Gly His Asp Pro His
 65                  70                  75                  80

Ile Leu Tyr Thr Leu Ser Ala Val Gln Val Leu Ser Leu Phe Asp Lys
                 85                  90                  95

Leu Asp Val Ile Asp Val Asp Lys Val Thr Ser Tyr Ile Val Ser Leu
            100                 105                 110

Gln Asn Glu Asp Gly Ser Phe Ser Gly Asp Met Trp Gly Glu Val Asp
        115                 120                 125

Thr Arg Phe Ser Tyr Ile Ala Ile Cys Cys Leu Ser Ile Leu His Arg
    130                 135                 140

Leu Asp Lys Ile Asn Val Glu Lys Ala Val Lys Tyr Ile Ile Ser Cys
145                 150                 155                 160

Lys Asn Met Asp Gly Gly Phe Gly Cys Thr Pro Gly Gly Glu Ser His
                165                 170                 175

Ala Gly Gln Ile Phe Cys Cys Val Gly Ala Leu Ala Ile Thr Gly Ser
            180                 185                 190

Leu Asp Leu Val Asp Lys Asp Leu Leu Gly Trp Trp Leu Cys Glu Arg
        195                 200                 205

Gln Val Lys Ser Gly Gly Leu Asn Gly Arg Pro Glu Lys His Pro Asp
```

```
      210             215             220
Val Cys Tyr Ser Trp Trp Val Leu Ser Ser Leu Ile Met Ile Asp Arg
225             230             235             240

Val His Trp Ile Ser Lys Glu Lys Leu Ile Lys Phe Ile Leu Asp Cys
                245             250             255

Gln Asp Thr Glu Asn Gly Gly Ile Ser Asp Arg Pro Asp Asp Ala Val
            260             265             270

Asp Val Phe His Thr Phe Phe Gly Val Ala Gly Leu Ser Leu Leu Glu
        275             280             285

Tyr Pro Gly Leu Lys Pro Val Asp Pro Ala Tyr Ala Leu Pro Val Asp
    290             295             300

Val Val Asn Arg Ile Ile Phe Thr Lys
305             310
```

<210> SEQ ID NO 5
<211> LENGTH: 1230
<212> TYPE: DNA
<213> ORGANISM: Triticum aestivum

<400> SEQUENCE: 5

```
tcaagctatg catccaacgc gttgggagct ctcccatatg gtcgacctgc aggcggccgc     60
gaattcacta gtgattagcg tggtcgcggc cgaggtcgtc gactggatca tgtcgtgcta    120
ccacccggaa tctggtgggt tcgggggaa cgtggggcac gacccgcatg tcctctacac    180
gctcagcacc gtgcaggtcc tctgcctctt cgatcggctc gatgttcttg atgcagacaa    240
aattgctgat tatattactg gacttcagaa tgaggatgga tcattttctg gtgatatttg    300
gggtgaagtt gatactaggt tctcttatat ttccatatgc accttgtcat tactgcatcg    360
tctgcacaaa attaatgtgg acaaggctgt agaatatatt gttagctgta agaacttgga    420
cggcgggttt ggagcgatgc cgggagggga gtctcatgct gggcagatat tctgttgtgt    480
tggtgctctc gcaatcaccg gctctttgca tcacattgat agagatctcc ttggatggtg    540
gctttgtgag cgccagtgta gagatggggg gctcaatggg cgtcctgaga acttgctga    600
tgtgtgctac tcatggtggg tgttatcaag cttgataatt attgatagag tgcactggat    660
tgacaaggaa aaacttgcaa agttcatatt gaactgtcag gacaaggaaa atggtggaat    720
ttcagataga ccagataatg cggtcgatat ctaccacacg tactttggag ttgcagggct    780
ctcattgatg gagtatcctg gagtgaagcc tatggatcct gcctacgccc tccctttaga    840
tgttgtcaac aggatcttct tgacaaaaca acaatagtgt gccttagcta ggaagatcat    900
gttgtaacgg cgttgacgtc aggtcagcac gagtggagag cttaccccctc cttcggtagc    960
tcgcgctgat gtttctgatc actcccatgc atgagatcat ggctttgaac gctcgatgat   1020
atagtgcaga cctcatattt accaggaaat ccggacactt gttatgtaga agagtgtaac   1080
gtccaaggac tgagaatcaa attcaatcaa gattattctt gttggaaaaa aaaaaaaaaa   1140
aaaaaaaaaa aaaactcga cctgcccggg cggccgctcg aaatcgaatt cccgcggccg   1200
ccatggcggc cgggagcatg cgacgtcggg                                   1230
```

<210> SEQ ID NO 6
<211> LENGTH: 291
<212> TYPE: PRT
<213> ORGANISM: Triticum aestivum

<400> SEQUENCE: 6

Gln Ala Met His Pro Thr Arg Trp Glu Leu Ser His Met Val Asp Leu

```
              1               5              10              15
           Gln Ala Ala Asn Ser Leu Val Ile Ser Val Ala Ala Glu Val
                            20              25              30
           Val Asp Trp Ile Met Ser Cys Tyr His Pro Glu Ser Gly Gly Phe Gly
                    35              40                  45
           Gly Asn Val Gly His Asp Pro His Val Leu Tyr Thr Leu Ser Thr Val
                50              55                  60
           Gln Val Leu Cys Leu Phe Asp Arg Leu Asp Val Leu Asp Ala Asp Lys
            65              70                  75              80
           Ile Ala Asp Tyr Ile Thr Gly Leu Gln Asn Glu Asp Gly Ser Phe Ser
                        85                  90                  95
           Gly Asp Ile Trp Gly Glu Val Asp Thr Arg Phe Ser Tyr Ile Ser Ile
                    100                 105                 110
           Cys Thr Leu Ser Leu Leu His Arg Leu His Lys Ile Asn Val Asp Lys
                    115                 120                 125
           Ala Val Glu Tyr Ile Val Ser Cys Lys Asn Leu Asp Gly Gly Phe Gly
                    130                 135                 140
           Ala Met Pro Gly Gly Glu Ser His Ala Gly Gln Ile Phe Cys Cys Val
           145             150                 155                 160
           Gly Ala Leu Ala Ile Thr Gly Ser Leu His His Ile Asp Arg Asp Leu
                        165                 170                 175
           Leu Gly Trp Trp Leu Cys Glu Arg Gln Cys Arg Asp Gly Gly Leu Asn
                        180                 185                 190
           Gly Arg Pro Glu Lys Leu Ala Asp Val Cys Tyr Ser Trp Trp Val Leu
                    195                 200                 205
           Ser Ser Leu Ile Ile Ile Asp Arg Val His Trp Ile Asp Lys Glu Lys
           210                 215                 220
           Leu Ala Lys Phe Ile Leu Asn Cys Gln Asp Lys Glu Asn Gly Gly Ile
           225                 230                 235                 240
           Ser Asp Arg Pro Asp Asn Ala Val Asp Ile Tyr His Thr Tyr Phe Gly
                        245                 250                 255
           Val Ala Gly Leu Ser Leu Met Glu Tyr Pro Gly Val Lys Pro Met Asp
                        260                 265                 270
           Pro Ala Tyr Ala Leu Pro Leu Asp Val Val Asn Arg Ile Phe Leu Thr
                    275                 280                 285
           Lys Gln Gln
               290

<210> SEQ ID NO 7
<211> LENGTH: 1422
<212> TYPE: DNA
<213> ORGANISM: Glycine max

<400> SEQUENCE: 7
gcacgaggtt ctgattctga tttctcacta gtaaaattga ggatcggcat tcagcaatga      60
tgaattccac agaagaagag tatcgtggct gcgagattat ggagaaagat gttcatgtca     120
cgtttctcga gttaatgtac tatttactcc catctccgta cgagtcccaa gagatcaacc     180
atctcactct cgcttacttt gtcatctctg gacttgacat cctcgactct ctccacaaag     240
ttgcgaagga tgctgttgtc agttgggttt tgtccttcca agctcacccc ggtgccaaga     300
ctgatctcaa tgatgggcaa ttctatggct tcatggatc caaaacttca cagtttcctc     360
cagatgagaa tggggttttg attcacaaca acagtcactt ggcaagtact tattgtgcca     420
tttccatatt gaaaattgtt ggttatgaat tgtccaatct tgactctgaa acaattgtga     480
```

-continued

```
cttctatgag gaaccttcaa cagcctgatg aagtttcat tccgattcat actggaggcg      540
aaacagatct taggtttgtg tattgtgcag ctgccatctg tttcatgttg gataactgga      600
gtggcatgga caaggagaaa accaaggatt acatattacg ttgccagtct tatgatggtg      660
gctttggatt agttcctggt gcagaatcgc atggaggtgc aacttattgt gctatggcat      720
ctctccgatt aatgggattc attgaagata atattctctc aagttgtgct tcatcttctt      780
tgatagatgc gccattgctg ctggactgga tcttgcagag gcagggaact gatggggggtt      840 ttcaaggtag accaaataaa tctagcgata catgttatgc attttggatt ggagccgttt      900
taaggatttt gggggggcttc aaatttgttg acaataaggc tctacgtgga ttttttgcttt      960 cttgtcaata taagtatggt ggtttcagca aattccctgg ggagtatcca gacctatacc     1020
actcctacta tggattcact gctttcagcc tgttggaaga atctggcttg aaatcacttt     1080
tttcggaact gggaatcact gaaaatgctg cactggcact ctagcttaga ttcagaaatg     1140
gatgtacctt tatacctgac atttcttaca tattatatga acctctcagc actaatccac     1200
tcttactgga cttttttttt tattctttca caaatttagg tggagtgtaa attttccatt     1260
tcatttgatt gtatttgtgt gcattaattc aggtaattgg acctcttcta tttagaacaa     1320
gctttttttg tattgctttc ttttgtttt atttacatttt cgatgaagtt tattattgaa     1380
tatgttaatt tgaagttcag cataaaaaaa aaaaaaaaa aa                         1422
```

<210> SEQ ID NO 8
<211> LENGTH: 355
<212> TYPE: PRT
<213> ORGANISM: Glycine max

<400> SEQUENCE: 8

```
Met Met Asn Ser Thr Glu Glu Tyr Arg Gly Cys Glu Ile Met Glu
  1               5                  10                  15

Lys Asp Val His Val Thr Phe Leu Glu Leu Met Tyr Tyr Leu Leu Pro
                 20                  25                  30

Ser Pro Tyr Glu Ser Gln Glu Ile Asn His Leu Thr Leu Ala Tyr Phe
             35                  40                  45

Val Ile Ser Gly Leu Asp Ile Leu Asp Ser Leu His Lys Val Ala Lys
 50                  55                  60

Asp Ala Val Val Ser Trp Val Leu Ser Phe Gln Ala His Pro Gly Ala
 65                  70                  75                  80

Lys Thr Asp Leu Asn Asp Gly Gln Phe Tyr Gly Phe His Gly Ser Lys
                 85                  90                  95

Thr Ser Gln Phe Pro Pro Asp Glu Asn Gly Val Leu Ile His Asn Asn
            100                 105                 110

Ser His Leu Ala Ser Thr Tyr Cys Ala Ile Ser Ile Leu Lys Ile Val
        115                 120                 125

Gly Tyr Glu Leu Ser Asn Leu Asp Ser Glu Thr Ile Val Thr Ser Met
    130                 135                 140

Arg Asn Leu Gln Gln Pro Asp Gly Ser Phe Ile Pro Ile His Thr Gly
145                 150                 155                 160

Gly Glu Thr Asp Leu Arg Phe Val Tyr Cys Ala Ala Ile Cys Phe
                165                 170                 175

Met Leu Asp Asn Trp Ser Gly Met Asp Lys Glu Lys Thr Lys Asp Tyr
            180                 185                 190

Ile Leu Arg Cys Gln Ser Tyr Asp Gly Gly Phe Gly Leu Val Pro Gly
        195                 200                 205
```

```
Ala Glu Ser His Gly Gly Ala Thr Tyr Cys Ala Met Ala Ser Leu Arg
    210                 215                 220

Leu Met Gly Phe Ile Glu Asp Asn Ile Leu Ser Ser Cys Ala Ser Ser
225                 230                 235                 240

Ser Leu Ile Asp Ala Pro Leu Leu Asp Trp Ile Leu Gln Arg Gln
            245                 250                 255

Gly Thr Asp Gly Gly Phe Gln Gly Arg Pro Asn Lys Ser Ser Asp Thr
            260                 265                 270

Cys Tyr Ala Phe Trp Ile Gly Ala Val Leu Arg Ile Leu Gly Gly Phe
            275                 280                 285

Lys Phe Val Asp Asn Lys Ala Leu Arg Gly Phe Leu Leu Ser Cys Gln
            290                 295                 300

Tyr Lys Tyr Gly Gly Phe Ser Lys Phe Pro Gly Glu Tyr Pro Asp Leu
305                 310                 315                 320

Tyr His Ser Tyr Tyr Gly Phe Thr Ala Phe Ser Leu Leu Glu Glu Ser
                325                 330                 335

Gly Leu Lys Ser Leu Phe Ser Glu Leu Gly Ile Thr Glu Asn Ala Ala
            340                 345                 350

Leu Ala Leu
        355

<210> SEQ ID NO 9
<211> LENGTH: 2335
<212> TYPE: DNA
<213> ORGANISM: Oryza sativa

<400> SEQUENCE: 9
gcacgagctt acacggcagc gtgcgcagga ggagaaaatt gcggagggga tccacagttc      60
cagccgcgtg tgacggcggc gtgcggttgc cgcggcgtgc tgctcgagcc gctttacgac     120
tgatccgagc ggctttttcc ggcgatcatg gcggacgcgc ccgccaccgg cggcggattc     180
cccgcgcagg actaccccac catcgacccc acctcgttcg acgtggtcct ctgcggcacc     240
ggcctcccgg agtccgtcct cgccgccgcc tgcgccgccg ccgggaagac ggtcctccac     300
gtcgacccca cccttttcta cggctccctc ttctcctccc tccctctccc ttccctcccc     360
tccttcctct cccccctcccc ctccgacgac cccgcccccct cccttccccc ctcctccgcc     420
gccgccgtcg atctccgccg ccgcagcccg tactcggagg tggagacctc ggggcggtg      480 cccgagccgt ccaggcgctt caccgccgac ctggtgggcc ccaggctgct ctactgcgcc     540
gacgaggccg tcgacctcct cctcaggtca gggggaagcc accatgtgga gttcaagagc     600 gtggagggg gaaccctcct ctactgggac ggcgatctct acccggtgcc ggactcgagg     660
caggccatct tcaaggacac caccctccag ctcagggaga gaacctact cttcaggttc     720 ttcaagcttg tgcaggccca cattgccgcg tcggctgccg gcgccgccgc ggcgggggaa     780
ggcgaggcct ccggtaggct gcccgatgag gacctggacc tccccttcgt cgaattcctc     840
aagaggcaga atctttcgcc caagatgaga gcggttgtct tgtatgcaat tgccatggcg     900
gattatgatc aggatggtgt ggagtcttgt gagaggttgt taacaacgag agagggagtc     960
aagacaattg ctctttactc ctcatctatt ggaggtttg ctaatgcaga gggggctttc    1020
atttatccta tgtatgggca tggtgagctg cctcaagctt tctgccgctg tgctgctgtt    1080
aaaggtgccc tatatgtatt gcgaatgcca gccacagcac ttcttgttga tgaggaaaaa    1140
aagcgttatg taggtatcag attggcatct ggtcaggata ttttgtgcca acagttgata    1200
```

-continued

```
ctcgatccat catatgaaat tccttccttg gatatgccaa gtgatgcacc agtatcaaat    1260
ttgccaagaa aagttgctag gggaatatgc ataatcagca gctctgtgag acaagataca    1320
tcaaatgttc tggttgtttt cccccaaag tcactagaag aggagcaaat tactgctgtt     1380
cgggtgcttc agttgagcag caatttagca gtatgccctc ctggaatgtt catggcatat    1440
ctctctactc cctgtactga tgccttcact ggaaagaaat gcatcagcaa agcaatagat    1500
gctcttttct caactaaggt ttctaatgat ttggaagatc atttggagaa aaacagtgaa    1560
gaaaataagg agagtgtgaa gccaacccta ctctggagct gtgtgtatgt acaagagatt    1620
atacagggaa catctggtac tgcattgtca tgccccatac ctgatgaaaa tatggactac    1680
aggagtatac ttgaatcaac aaaaatgctg ttcactgata tttgtcctaa tgaagagttc    1740
ctgcctagaa attcagctcc caaatatgct tctgataatg actctgattc tgcagagtaa    1800
atccaaactt gcaagggct ttgtattcta catgacaggg ttatcgttga agatatctgt     1860
tccatattac agtgttcccc aaagtcacgg taagaaatat tgcagcaagg gggagcccttt   1920 tacgttggtg agatttgcca ggtttctctt tgactagatt gcagatgcct acattgttcc    1980
atcattggta cgacatatta tgatactggt aaaacactca agagagagcg atgcagatgt    2040
ccttggcatt ttgacatttg gagaacatca taccacatga accgcttagt gtgattacta    2100
catccatatg gttctctgaa ttctatgctg aatttgttgg cacataggag tactgtacta    2160
cataggaagg atactgctga gttctatgct aaatctgtgt attttttggtg ggctgcctga   2220 atcattgtac aagcgaacga cagaaatgga tatcaaatga ggtccctccg agagggagtt   2280
gcattacatg catccttatc gatctgcgcg gtcaaaaaaa aaaaaaaaaa aaaaa         2335
```

<210> SEQ ID NO 10
<211> LENGTH: 550
<212> TYPE: PRT
<213> ORGANISM: Oryza sativa

<400> SEQUENCE: 10

```
Met Ala Asp Ala Pro Ala Thr Gly Gly Gly Phe Pro Ala Gln Asp Tyr
  1               5                  10                  15

Pro Thr Ile Asp Pro Thr Ser Phe Asp Val Val Leu Cys Gly Thr Gly
                 20                  25                  30

Leu Pro Glu Ser Val Leu Ala Ala Cys Ala Ala Gly Lys Thr
             35                  40                  45

Val Leu His Val Asp Pro Asn Pro Phe Tyr Gly Ser Leu Phe Ser Ser
 50                  55                  60

Leu Pro Leu Pro Ser Leu Pro Ser Phe Leu Ser Pro Ser Pro Ser Asp
 65                  70                  75                  80

Asp Pro Ala Pro Ser Pro Ser Pro Ser Ser Ala Ala Val Asp Leu
                 85                  90                  95

Arg Arg Arg Ser Pro Tyr Ser Glu Val Glu Thr Ser Gly Ala Val Pro
                100                 105                 110

Glu Pro Ser Arg Arg Phe Thr Ala Asp Leu Val Gly Pro Arg Leu Leu
            115                 120                 125

Tyr Cys Ala Asp Glu Ala Val Asp Leu Leu Arg Ser Gly Gly Ser
        130                 135                 140

His His Val Glu Phe Lys Ser Val Glu Gly Gly Thr Leu Leu Tyr Trp
145                 150                 155                 160

Asp Gly Asp Leu Tyr Pro Val Pro Asp Ser Arg Gln Ala Ile Phe Lys
                165                 170                 175
```

```
Asp Thr Thr Leu Gln Leu Arg Glu Lys Asn Leu Leu Phe Arg Phe Phe
            180                 185                 190

Lys Leu Val Gln Ala His Ile Ala Ala Ser Ala Ala Gly Ala Ala Ala
        195                 200                 205

Ala Gly Glu Gly Glu Ala Ser Gly Arg Leu Pro Asp Glu Asp Leu Asp
    210                 215                 220

Leu Pro Phe Val Glu Phe Leu Lys Arg Gln Asn Leu Ser Pro Lys Met
225                 230                 235                 240

Arg Ala Val Val Leu Tyr Ala Ile Ala Met Ala Asp Tyr Asp Gln Asp
                245                 250                 255

Gly Val Glu Ser Cys Glu Arg Leu Leu Thr Arg Glu Gly Val Lys
            260                 265                 270

Thr Ile Ala Leu Tyr Ser Ser Ile Gly Arg Phe Ala Asn Ala Glu
            275                 280                 285

Gly Ala Phe Ile Tyr Pro Met Tyr Gly His Gly Glu Leu Pro Gln Ala
            290                 295                 300

Phe Cys Arg Cys Ala Ala Val Lys Gly Ala Leu Tyr Val Leu Arg Met
305                 310                 315                 320

Pro Ala Thr Ala Leu Leu Val Asp Glu Glu Lys Lys Arg Tyr Val Gly
                325                 330                 335

Ile Arg Leu Ala Ser Gly Gln Asp Ile Leu Cys Gln Gln Leu Ile Leu
            340                 345                 350

Asp Pro Ser Tyr Glu Ile Pro Ser Leu Asp Met Pro Ser Asp Ala Pro
            355                 360                 365

Val Ser Asn Leu Pro Arg Lys Val Ala Arg Gly Ile Cys Ile Ile Ser
            370                 375                 380

Ser Ser Val Arg Gln Asp Thr Ser Asn Val Leu Val Phe Pro Pro
385                 390                 395                 400

Lys Ser Leu Glu Glu Glu Gln Ile Thr Ala Val Arg Val Leu Gln Leu
                405                 410                 415

Ser Ser Asn Leu Ala Val Cys Pro Pro Gly Met Phe Met Ala Tyr Leu
            420                 425                 430

Ser Thr Pro Cys Thr Asp Ala Phe Thr Gly Lys Lys Cys Ile Ser Lys
            435                 440                 445

Ala Ile Asp Ala Leu Phe Ser Thr Lys Val Ser Asn Asp Leu Glu Asp
    450                 455                 460

His Leu Glu Lys Asn Ser Glu Glu Asn Lys Glu Ser Val Lys Pro Thr
465                 470                 475                 480

Leu Leu Trp Ser Cys Val Tyr Val Gln Glu Ile Ile Gln Gly Thr Ser
                485                 490                 495

Gly Thr Ala Leu Ser Cys Pro Ile Pro Asp Glu Asn Met Asp Tyr Arg
            500                 505                 510

Ser Ile Leu Glu Ser Thr Lys Met Leu Phe Thr Asp Ile Cys Pro Asn
            515                 520                 525

Glu Glu Phe Leu Pro Arg Asn Ser Ala Pro Lys Tyr Ala Ser Asp Asn
            530                 535                 540

Asp Ser Asp Ser Ala Glu
545                 550

<210> SEQ ID NO 11
<211> LENGTH: 1359
<212> TYPE: DNA
<213> ORGANISM: Triticum aestivum

<400> SEQUENCE: 11
```

-continued

```
gcacgagagg acttggacct cccctttatt gaattcctca agaaacagca gcttcaaccc      60
aagattagag cggttgtgct atatgcaatt gccatggcag attatgatca agatgccgca     120
gacacatgcg agaaattgct aacaacaaga gatggaatca agaccctagc tctttattcc     180
tcgtccattg ggaggtttgc taatgcccaa ggtgctttca tttatcctat gtacgggcat     240
ggtgagctac tgcaagcttt ctgtcgcttt gctgctgtta agggtgccct atatgtgttg     300
cggatgccag tcacagccct cctcgtggac caggaaaaga agcgttatat aggcaccaga     360
ttggcttctg gtcaggatat tttgtgccag cagttgatac ttggtccctc gtacaaaatt     420
ccttcattgg acatgccatc tgatgcttca gactcaaact tgacgagaaa agttgccagg     480
ggagtatgca taatcagcag ctccataaaa gaggcttcat caaatgttct ggttgttttc     540
cccccaaaat cattacaaga gcagcaagct acagctgttc gggcgcttca gctgagcagc     600
aatgtagcag tatgccctcc tggaatgttc atggtatatc tgtctactcc ctgtactgat     660
gcctttacgg gaaagcagta cataaacaag gcaatggagg ttcttttcag tactcaggct     720
tcagatgatt cagaaggcca tttgagagaca accagcaaaa acatcgagga tagaaagcca     780
gtgctaatct ggagttgtgt gtatgttcaa gagatcacac agggaacatc tggtgctgta     840
ttgtcatgcc ccatgccgga tgaaaacctg gactacagag atatactgga atcgacaaaa     900
cagttattta cagatattta tcctgacgaa gaattcctgc ctagaaacgc aactcctaaa     960
tatgccgacg atgactctga tcttgcagag tagaaacatg tttgcagagg ttagtgttt    1020
ttctggacaa atattccaca agagatacat gaaggcattt tagatacatc gcaccaacat    1080
ggatgatctg ctcagtgagc gagaccacag acaacgttga tggttgtatg gcttgttgca    1140
gtgcctgtag ttattactgc acaagctaca tgtggcgcct ttcgtttgtt gcactggttc    1200
ttgctacatg tggcgccttt catttgttgc actggttctt tgtacgagtg aaacagagta    1260
atgaaattga gtttaaacta cttgtctgat gcaaaaaaaa aaaaaaaaaa aaaaaaaaaa    1320
aaaaaaaaaa aaaaaaaaaa aaaaaaaaaa aaaaaaaaa                           1359
```

<210> SEQ ID NO 12
<211> LENGTH: 330
<212> TYPE: PRT
<213> ORGANISM: Triticum aestivum

<400> SEQUENCE: 12

```
Ala Arg Glu Asp Leu Asp Leu Pro Phe Ile Glu Phe Leu Lys Lys Gln
  1               5                  10                  15

Gln Leu Gln Pro Lys Ile Arg Ala Val Val Leu Tyr Ala Ile Ala Met
             20                  25                  30

Ala Asp Tyr Asp Gln Asp Ala Ala Asp Thr Cys Glu Lys Leu Leu Thr
         35                  40                  45

Thr Arg Asp Gly Ile Lys Thr Leu Ala Leu Tyr Ser Ser Ser Ile Gly
     50                  55                  60

Arg Phe Ala Asn Ala Gln Gly Ala Phe Ile Tyr Pro Met Tyr Gly His
 65                  70                  75                  80

Gly Glu Leu Leu Gln Ala Phe Cys Arg Phe Ala Ala Val Lys Gly Ala
                 85                  90                  95

Leu Tyr Val Leu Arg Met Pro Val Thr Ala Leu Leu Val Asp Gln Glu
            100                 105                 110

Lys Lys Arg Tyr Ile Gly Thr Arg Leu Ala Ser Gly Gln Asp Ile Leu
        115                 120                 125
```

-continued

```
Cys Gln Gln Leu Ile Leu Gly Pro Ser Tyr Lys Ile Pro Ser Leu Asp
    130                 135                 140

Met Pro Ser Asp Ala Ser Asp Ser Asn Leu Thr Arg Lys Val Ala Arg
145                 150                 155                 160

Gly Val Cys Ile Ile Ser Ser Ser Ile Lys Glu Ala Ser Ser Asn Val
                165                 170                 175

Leu Val Val Phe Pro Pro Lys Ser Leu Gln Glu Gln Gln Ala Thr Ala
            180                 185                 190

Val Arg Ala Leu Gln Leu Ser Ser Asn Val Ala Val Cys Pro Pro Gly
        195                 200                 205

Met Phe Met Val Tyr Leu Ser Thr Pro Cys Thr Asp Ala Phe Thr Gly
    210                 215                 220

Lys Gln Tyr Ile Asn Lys Ala Met Glu Val Leu Phe Ser Thr Gln Ala
225                 230                 235                 240

Ser Asp Asp Ser Glu Gly His Leu Glu Thr Thr Ser Lys Asn Ile Glu
                245                 250                 255

Asp Arg Lys Pro Val Leu Ile Trp Ser Cys Val Tyr Val Gln Glu Ile
            260                 265                 270

Thr Gln Gly Thr Ser Gly Ala Val Leu Ser Cys Pro Met Pro Asp Glu
        275                 280                 285

Asn Leu Asp Tyr Arg Asp Ile Leu Glu Ser Thr Lys Gln Leu Phe Thr
    290                 295                 300

Asp Ile Tyr Pro Asp Glu Glu Phe Leu Pro Arg Asn Ala Thr Pro Lys
305                 310                 315                 320

Tyr Ala Asp Asp Asp Ser Asp Leu Ala Glu
                325                 330
```

PLANT GERANYLGERANYL TRANSFERASES

This application claims priority benefit of U.S. Provisional Application Ser. No. 60/098,743 filed Sep. 1, 1998, now pending.

FIELD OF THE INVENTION

This invention is in the field of plant molecular biology. More specifically, this invention pertains to nucleic acid fragments encoding geranylgeranyl transferase subunits in plants and seeds.

BACKGROUND OF THE INVENTION

Lipids and proteins associate covalently to form lipid-linked proteins and noncovalently to form lipoproteins. The lipid portions of lipid-linked proteins anchor their attached proteins to membranes and mediate protein-protein interactions. Proteins form covalent attachments to lipids in several ways, one of which is the covalent attachment of isoprenoid groups, mainly the $C_{15}$ farnesyl and $C_{20}$ geranylgeranyl residues.

In mammals, geranylgeranyltransferase is known to catalyze the transfer of a geranyl-geranyl moiety from geranylgeranyl pyrophsophate to both cysteines in Rab proteins (Farnsworth, C. C. etal. (1994)*Proc Natl Acad Sci USA* 91(25):11963–11967) Rab proteins are Ras-related small GTPases that are geranylgeranylated on cysteine residues located at or near their C termini. Mammalian protein geranylgeranyl transferases types 1 and 2 are heterodimers composed of an alpha and beta subunit. The alpha subunit shows homology to the alpha subunits of a closely related enzyme, farnesyltransferase.

Farnesyltransferases have been described in pea, tomato, and Arabidopsis, but have not been described in monocots. The plant farnesyltransferases also consist of alpha and beta subunits. The geranylgeranyl transferase beta subunit belongs to the protein prenyltransferase beta subunit family. The beta subunits of the type 1 and 2 geranylgeranyltransferases have not been previously described in plants. Work done in yeast has established that geranylgeranyltransferases are distinct from the closely related farnesyltransferases.

The mammalian geranylgeranyl transferases require the aid of a RAB escort protein (also called component A). RAB escort protein is required for Rab geranylgeranyl transferase activity in mammals. RAB escort protein binds unprenylated RAB proteins, presents it to the catalytic component B (alpha/beta subunit complex of geranylgeranyltransferase). RAB binding protein remains bound to the prenylated protein after the geranylgeranyl transfer reaction. Component A may be regenerated by transferring its prenylated RAB to a protein acceptor.

There is a great deal of interest in identifying the genes that encode geranylgeranyl transferase in plants. These genes may be used in plant cells to control cell growth. Accordingly, the availability of nucleic acid sequences encoding all or a portion of geranylgeranyl transferase proteins would facilitate studies to better understand cell growth in plants, provide genetic tools to enhance cell growth in tissue culture, increase the efficiency of gene transfer and help provide more stable transformations. Geranylgeranyl transferase proteins may also provide targets to facilitate design and/or identification of inhibitors of cell growth that may be useful as herbicides.

SUMMARY OF THE INVENTION

The instant invention relates to isolated nucleic acid fragments encoding geranylgeranyl transferase subunits. Specifically, this invention concerns an isolated nucleic acid fragment encoding a geranylgeranyl transferase type I beta subunit, type II beta subunit or Rab escort protein and an isolated nucleic acid fragment that is substantially similar to an isolated nucleic acid fragment encoding a geranylgeranyl transferase type I beta subunit, type II beta subunit or Rab escort protein. In addition, this invention relates to a nucleic acid fragment that is complementary to the nucleic acid fragment encoding a geranylgeranyl transferase type I beta subunit, type II beta subunit or Rab escort protein.

An additional embodiment of the instant invention pertains to a polypeptide encoding all or a substantial portion of a geranylgeranyl transferase subunit selected from the group consisting of geranylgeranyl transferase type I beta subunit, type II beta subunit and Rab escort protein.

In another embodiment, the instant invention relates to a chimeric gene encoding a geranylgeranyl transferase type I beta subunit, type II beta subunit or Rab escort protein, or to a chimeric gene that comprises a nucleic acid fragment that is complementary to a nucleic acid fragment encoding a geranylgeranyl transferase type I beta subunit, type II beta subunit or Rab escort protein, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a geranylgeranyl transferase type I beta subunit, type II beta subunit or Rab escort protein, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a geranylgeranyl transferase type I beta subunit, type II beta subunit or Rab escort protein in a transformed host cell comprising: a) transforming a host cell with a chimeric gene comprising a nucleic acid fragment encoding a geranylgeranyl transferase type I beta subunit, type II beta subunit or Rab escort protein; and b) growing the transformed host cell under conditions that are suitable for expression of the chimeric gene wherein expression of the chimeric gene results in production of altered levels of geranylgeranyl transferase type I beta subunit, type II beta subunit or Rab escort protein in the transformed host cell.

An addition embodiment of the instant invention concerns a method for obtaining a nucleic acid fragment encoding all or a substantial portion of an amino acid sequence encoding a geranylgeranyl transferase type I beta subunit, type II beta subunit or Rab escort protein.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

Geranylgeranyl Transferase Subunits

| Protein | Clone Designation | SEQ ID NO: (Nucleotide) | SEQ ID NO: (Amino Acid) |
|---|---|---|---|
| Geranylgeranyl Transferase Type II Beta Subunit | cco1n.pk066.m2 | 1 | 2 |
| Geranylgeranyl Transferase Type II Beta Subunit | sf11.pk0074.b7 | 3 | 4 |
| Geranylgeranyl Transferase Type II Beta Subunit | w1su2.pk0001.h3 | 5 | 6 |
| Geranylgeranyl Transferase Type I Beta Subunit | sre.pk0040.h8 | 7 | 8 |
| Rab Escort Protein | r10n.pk0025.f10 | 9 | 10 |
| Rab Escort Protein | wr1.pk0001.c3 | 11 | 12 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6× SSC, 0.5% SDS at room temperature for 15 min, then repeated with 2× SSC, 0.5% SDS at 45° C. for 30 min, and then repeated twice with 0.2× SSC, 0.5% SDS at 50° C. for 30 min. A more preferred set of stringent conditions uses higher temperatures in which the washes are identical to those above except for the temperature of the final two 30 min washes in 0.2× SSC, 0.5% SDS was increased to 60° C. Another preferred set of highly stringent conditions uses two final washes in 0.1× SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed MRNA upstream of the translation start sequence. The translation leader sequence may affect processing of the primary transcript to MRNA, MRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting MRNA processing or gene expression. The polyadenylation signal is usually characterized by affecting the addition of polyadenylic acid tracts to the 3' end of the MRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the MRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of MRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several geranylgeranyl transferase subunits have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other geranylgeranyl transferase type I beta subunit, type II beta subunit or Rab escort protein, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the MRNA precursor encoding plant genes. Alternatively, the second primer sequence may be based upon sequences derived from the cloning vector. For example, the skilled artisan can follow the RACE protocol (Frohman et al. (1988) *Proc. Natl. Acad Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immuno.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of cell growth in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of MRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.*100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded geranylgeranyl transferase subunit. An example of a vector for high level expression of the instant polypeptides in a bacterial host is provided (Example 8).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein). In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 1 7:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries. Isolation and Sequencing of CDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cco1n | Corn cob of 67 day old plants grown in green house* | cco1n.pk066.m2 |
| r10n | Rice 15 day old leaf* | r10n.pk0025.f10 |
| sf11 | Soybean immature flower | sf11.pk0074.b7 |
| sre | Soybean root elongation zone 4 to 5 days after germination | sre.pk0040.h8 |
| w1su2 | Wheat WLMK8 cDNAs subtracted with WLM0 cDNAs** | w1su2.pk0001.h3 |
| wr1 | Wheat root from 7 day old seedling | wr1.pk0001.c3 |

*These libraries were normalized essentially as described in U.S. Pat. No. 5,482,845, incorporated herein by reference.
**WLMK8 cDNAs are from wheat seedlings 8 hours after inoculation with *Erysiphe graminis f. sp tritici* and treatment with 6-iodo-2-propoxy-3-propyl-4(3H)-quinazolinone (synthesis and methods of using this compound are described in USSN 08/545,827, incorporated herein by reference). WLM0 cDNAs are from wheat seedlings 0 hours after inoculation with *Erysiphe graminis f. sp tritici*. Subtraction of the cDNA libraries was achieved using a combination of a cDNA synthesis kit (Strategene: cat # 200400) and the Clontech PCR-Select cDNA Subtraction it (Clontech, cat # PT3138-1) as per manufactures instructions.

cDNA libraries may be prepared by any one of many methods available. For example, the cDNAs may be introduced into plasmid vectors by first preparing the CDNA libraries in Uni-ZAP™ XR vectors according to the manufacturer's protocol (Stratagene Cloning Systems, La Jolla, Calif.). The Uni-ZAPT™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert CDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding geranylgeranyl transferase subunits were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Geranylgeranyl Transferase

Type II Beta Subunit

The BLASTX search using the EST sequences from clones listed in Table 3 revealed similarity of the polypeptides encoded by the cDNAs to geranylgeranyl transferase type II beta subunit from Homo sapiens (NCBI Identifier No. gi 2506788). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Homo sapiens* Geranylgeranyl Transferase Type II Beta Subunit

| Clone | Status | BLAST pLog Score to gi 2506788 |
|---|---|---|
| cco1n.pk066.m2 | FIS | 106.00 |
| sf11.pk0074.b7 | FIS | 117.00 |
| w1su2.pk0001.h3 | FIS | 96.70 |

The data in Table 4 represents a calculation of the percent identity of the amino acid sequences set forth in SEQ ID NOs:2, 4 and 6 and the Homo sapiens sequence. The percent identity between the amino acid sequences set forth in SEQ ID NOs:2, 4 and 6 ranges between 71%–82%.

TABLE 4

Percent Identity of Amino Acid Sequences Deduced From the Nucleotide Sequences of cDNA Clones Encoding Polypeptides Homologous to *Homo sapiens* Geranylgeranyl Transferase Type II Beta Subunit

| SEQ ID NO. | Percent Identity to gi 2506788 |
|---|---|
| 2 | 11% |
| 4 | 12% |
| 6 | 11% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Sequence alignments and BLAST scores and probabilities indicate that the nucleic acid fragments comprising the instant cDNA clones encode a substantial portion of a geranylgeranyl transferase type II beta subunit. These sequences represent the first corn, soybean and wheat sequences encoding geranylgeranyl transferase type II beta subunit.

Example 4

Characterization of cDNA Clones Encoding Geranylgeranyl Transferase Type I Beta Subunit The BLASTX search using the EST sequence from the clone listed in Table 5 revealed similarity of the polypeptide encoded by the cDNA to geranylgeranyl transferase type I beta subunit from *Arabidopsis thaliana* (NCBI Identifier No. gi 3355484). Shown in Table 5 are the BLAST results for individual ESTs ("EST"), the sequences of the entire cDNA inserts comprising the indicated cDNA clones ("FIS"), or contigs assembled from two or more ESTs ("Contig"):

TABLE 5

BLAST Results for Sequences Encoding Polypeptides Homologous to *Arabidopsis thaliana* Geranylgeranyl Transferase Type I Beta Subunit

| Clone | Status | BLAST pLog Score to gi 3355484 |
| --- | --- | --- |
| sre.pk0040.h8 | FIS | 139.00 |

The data in Table 6 represents a calculation of the percent identity of the amino acid sequence set forth in SEQ ID NO:8 and the Arabidopsis thaliana sequence.

TABLE 6

Percent Identity of Amino Acid Sequences Deduced From the Nucleotide Sequences of cDNA Clones Encoding Polypeptides Homologous to *Arabidopsis thaliana* Geranylgeranyl Transferase Type I Beta Subunit

| SEQ ID NO. | Percent Identity to gi 3355484 |
| --- | --- |
| 8 | 65% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a geranylgeranyl transferase type I beta subunit. These sequences represent the first soybean sequence encoding geranylgeranyl transferase type I beta subunit.

Example 5

Characterization of cDNA Clones Encoding Rab Escort Protein

The BLASTX search using the EST sequences from the clones listed in Table 7 revealed similarity of the polypeptides encoded by the cDNAs to Rab escort protein from Homo sapiens (NCBI Identifier No. gi 2950156). Shown in Table 7 are the BLAST results for individual ESTs ("EST"), the sequences of the entire cDNA inserts comprising the indicated cDNA clones ("FIS"), or contigs assembled from two or more ESTs ("Contig"):

TABLE 7

BLAST Results for Sequences Encoding Polypeptides Homologous to *Homo sapiens* Rab Escort Protein

| Clone | Status | BLAST pLog Score to gi 2950156 |
| --- | --- | --- |
| r10n.pk0025.f10 | FIS | 41.04 |
| wr1.pk0001.c3 | FIS | 29.22 |

The data in Table 8 represents a calculation of the percent identity of the amino acid sequence set forth in SEQ ID NO:9 and 10 and the Homo sapiens sequence. The percent identity between the amino acid sequence set forth in SEQ ID NO:9 and 10 was 76%.

TABLE 8

Percent Identity of Amino Acid Sequences Deduced From the Nucleotide Sequences of cDNA Clones Encoding Polypeptides Homologous to *Homo sapiens* Rab Escort Protein

| SEQ ID NO. | Percent Identity to gi 3355484 |
| --- | --- |
| 9 | 19% |
| 10 | 21% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a Rab escort protein. These sequences represent the first rice and wheat sequences encoding Rab escort proteins.

Example 6

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL 1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of Agrobacterium tumefaciens.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated particles are then accelerated into the corn tissue with a Biolistic™ PDS-1 000/He (Bio-Rad gold particles can be placed in the center of a Kapton™ flying disc (Bio-Rad Labs). The Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 7

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 8

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 mn of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated nucleic acid fragment encoding a geranylgeranyl transferase type II beta subunit comprising a member selected from the group consisting of:
   (a) an isolated nucleic acid fragment encoding an amino acid sequence of at least 290 amino acids that is at least 70% identical to the amino acid sequence set forth in a member selected from the group consisting of SEQ ID NO:2, 4 and 6;
   (b) an isolated nucleic acid fragment that is complementary to (a).

2. The isolated nucleic acid fragment of claim 1 wherein the nucleic acid fragment is a functional RNA.

3. The isolated nucleic acid fragment of claim 1 wherein the nucleotide sequence of the fragment comprises the sequence set forth in a member selected from the group consisting of SEQ ID NO: 1, 3 and 5.

4. A chimeric gene comprising the nucleic acid fragment of claim 1 operably linked to suitable regulatory sequences.

5. A transformed host cell comprising the chimeric gene of claim 4.

6. An isolated nucleic acid fragment encoding a geranylgeranyl transferase type I beta subunit comprising a member selected from the group consisting of:
   (a) an isolated nucleic acid fragment encoding an amino acid sequence of at least 350 amino acids that is at least 70% identical to the amino acid sequence set forth in SEQ ID NO:8;
   (b) an isolated nucleic acid fragment that is complementary to (a).

7. The isolated nucleic acid fragment of claim 6 wherein the nucleic acid fragment is a functional RNA.

8. The isolated nucleic acid fragment of claim 6 wherein the nucleotide sequence of the fragment comprises the sequence set forth in SEQ ID NO:7.

9. A chimeric gene comprising the nucleic acid fragment of claim 6 operably linked to suitable regulatory sequences.

10. A transformed host cell comprising the chimeric gene of claim 9.

* * * * *